United States Patent
Lacey et al.

(10) Patent No.: US 7,102,308 B2
(45) Date of Patent: Sep. 5, 2006

(54) METHOD AND SYSTEM FOR A VARIABLE SPEED FAN CONTROL FOR THERMAL MANAGEMENT

(75) Inventors: Joseph James Lacey, Cambridge, WI (US); Ashutosh Joshi, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 230 days.

(21) Appl. No.: 10/710,213

(22) Filed: Jun. 25, 2004

(65) Prior Publication Data

US 2005/0287008 A1    Dec. 29, 2005

(51) Int. Cl.
*H02P 1/00* (2006.01)
(52) U.S. Cl. .................. 318/268; 318/471; 388/934
(58) Field of Classification Search ............ 318/471, 318/268, 934, 634; 700/299; 361/687; 378/19, 378/10
See application file for complete search history.

(56) References Cited

U.S. PATENT DOCUMENTS

| | | | |
|---|---|---|---|
| 4,969,167 A | 11/1990 | Zupancic et al. | 378/19 |
| 5,444,752 A | 8/1995 | Dobbs et al. | 378/19 |
| 6,385,292 B1 | 5/2002 | Dunham et al. | 278/122 |
| 6,723,970 B1 * | 4/2004 | Whipple, Jr. | 219/681 |
| 6,735,499 B1 | 5/2004 | Ohki et al. | 700/299 |
| 2003/0188538 A1 * | 10/2003 | Chu et al. | 62/3.2 |

* cited by examiner

*Primary Examiner*—Karen Masih
(74) *Attorney, Agent, or Firm*—Cantor Colburn LLP

(57) ABSTRACT

A method and system for variable speed fan control for thermal management of a device includes disposing a first temperature sensor proximate a variable speed fan to measure an air temperature of inlet air $T_{air}$ that cools the device by convection air flow. A controller is configured to compensate for changes in $T_{air}$ by varying a convection coefficient (h) which is a strong function of air velocity to maintain the product of $h*\Delta T$ at a constant value, wherein $\Delta T$ is a temperature differential between the device ($T_{AD}$) minus $T_{air}$. Thus, h is varied by varying air velocity by varying a speed of the variable speed fan.

31 Claims, 9 Drawing Sheets

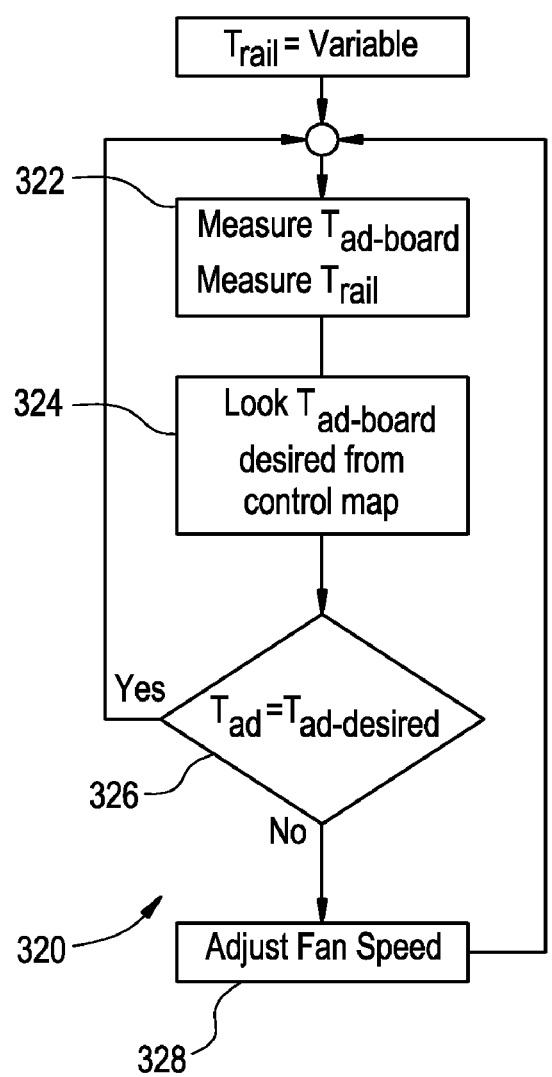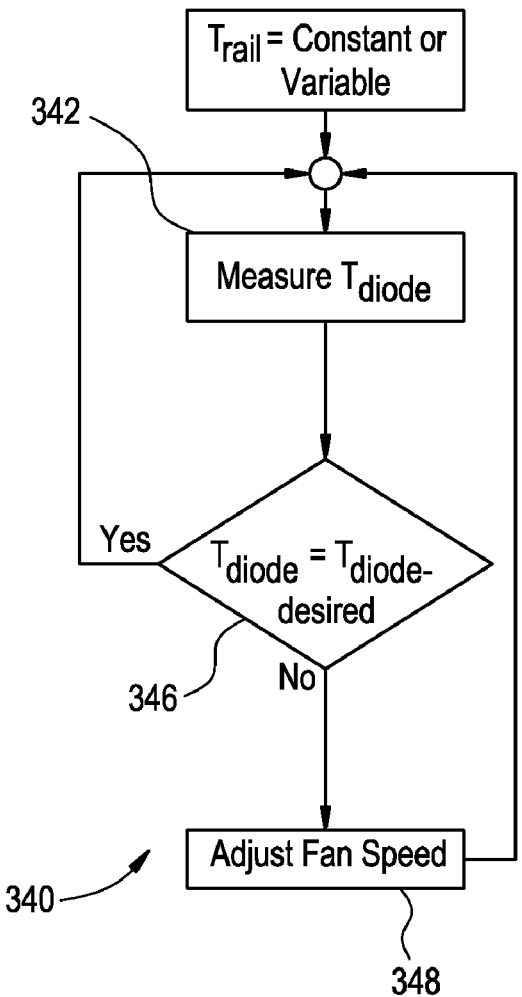
FIG. 14
Control Strategy 3
FIG. 15
Control Strategy 4

METHOD AND SYSTEM FOR A VARIABLE SPEED FAN CONTROL FOR THERMAL MANAGEMENT

BACKGROUND OF THE INVENTION

The present disclosure relates generally to a method for cooling a data acquisition system (DAS) and detectors associated with computer assisted tomography (CAT) and in particular, to a method for cooling a DAS/detectors in different air temperatures and air flow rates using a variable speed fan to compensate for rotation of the gantry.

The present disclosure pertains to the art of medical diagnostic imaging and more particularly to computerized tomographic (CT) scanners. The disclosure finds particular application in conjunction with cooling systems associated with CT scanners and will be described with particular reference thereto. It will be appreciated, however, that the invention has broader applications and may be advantageously employed in other environments.

CT scanner cooling systems of the type to which this invention pertains have ordinarily included air conditioning units housed within CT scanner gantries. Such air conditioning units were deemed necessary because they cooled sensitive radiation detectors and other components associated with the CT scanners. When a CT scanner is in operation, an X-ray beam rotates rapidly in a patient examination region. A rotating anode X-ray tube rotates continuously around the examination region and causes the beam to so rotate. The X-ray anode generates a significant amount of heat as well as the X-rays. Because the radiation detectors lose linearity and fail prematurely when heated, they are kept cool. A typical CT scanner cooling system uses an air conditioned sealed gantry to maintain radiation detectors at a proper working temperature.

The use of air conditioning systems in connection with CT scanners has several drawbacks. First, the air conditioning units take up valuable space within the CT scanner gantry. The units are relatively cumbersome, and limit the amount of space available for the various CT scanner features.

Second, air conditioning units require frequent maintenance. If the air conditioning unit breaks down, the detectors can overheat during CT scanner use. Further, the air conditioning units are not readily removable. Their position within a CT scanners makes it difficult to repair other CT scanner parts and features by inhibiting free access to such parts.

Currently, data acquisition system (DAS) cooling is also done with constant speed fans which are always on. A current integrated DAS/detector design is extremely sensitive to cooling air temperature control, air flow rate and rapid changes in cooling air flow rate and temperature. The most sensitive and therefore potentially useful detectors for this application are solid state devices made up of a scintillating crystal for converting the x-ray energy to light and a semiconductor photo-diode to convert the light to an electrical signal that can be computer processed. Unfortunately, however, both of these devices are temperature sensitive, with the photo diode responding exponentially to temperature. Operation of the x-ray source and power supplies generates a large amount of heat that causes the ambient temperature inside the CT system to rise significantly. Changes in A/D card temperatures are directly reflected in the diode temperatures operably connected to the A/D card. Accurate temperature control or compensation for each of the solid state detectors is therefore an important requirement.

It is a very difficult design challenge to control the air temperature variation within a gantry and is subject to a multitude of design constraints such as, room air temperature control, allowable system packaging volume in an existing CT gantry platform (e.g., major components and component placement not easily changed or modified). Current CT systems have air temperature variations (e.g., 15° C.) which are unacceptable for current DAS/detector design. Control of the air temperature and flow rate due to gantry rotations is an even more challenging design issue and is not addressed by current system designs and expected to get worse as system rotational speeds increase. Furthermore, current DAS cooling fans are loud and barely meet audible specifications for such fans.

Accordingly, a method and system to quietly cool a DAS/detector is desired that limits an air temperature variation in the gantry on the order of less than 15° C. and maintains cooling fan efficiency as the fan is rotated when the gantry is rotated.

BRIEF DESCRIPTION OF THE INVENTION

One aspect of the invention is a method for variable speed fan control for thermal management of a device. The method includes disposing a first temperature sensor proximate a variable speed fan; measuring an air temperature of inlet air $T_{air}$ that cools the device by convection air flow; and configuring a controller to compensate for changes in $T_{air}$ by varying a convection coefficient (h) which is a function of air velocity to maintain a product of $h*\Delta T$ at a constant value; wherein $\Delta T$ is a temperature differential between the device $(T_{AD})$ and $T_{air}$.

Another aspect of the invention is a method for variable speed fan control for thermal management of a A/D card in an imaging system. The method includes: disposing a variable speed fan configured to convectively cool the A/D card for the CT scanner for a data acquisition system (DAS) in operable communication with a plurality of detectors; disposing a first temperature sensor proximate the variable speed fan; measuring an air temperature of inlet air $T_{air}$ that cools the A/D card by convection air flow; and configuring a controller to compensate for changes in $T_{air}$ by varying a convection coefficient (h) which is a function of air velocity to maintain a product of $h*\Delta T$ at a constant value; wherein $\Delta T$ is a temperature differential between the A/D card $(T_{AD})$ and $T_{air}$.

A further aspect of the invention is a system for variable speed fan control for thermal management of a device includes disposing a first temperature sensor proximate a variable speed fan to measure an air temperature of inlet air $T_{air}$ that cools the device by convection air flow. A controller is configured to compensate for changes in $T_{air}$ by varying a convection coefficient (h) which is a strong function of air velocity to maintain the product of $h*\Delta T$ at a constant value, wherein $\Delta T$ is a temperature differential between the device $(T_{AD})$ minus $T_{air}$. Thus, h is varied by varying air velocity by varying a speed of the variable speed fan.

Lastly, a computer program product for variable speed fan control for thermal management of a device is disclosed. The product includes: a storage medium readable by a processing circuit and storing instructions for execution by the processing circuit for: reading a first temperature sensor proximate a variable speed fan, the sensor configured to measure an air temperature of inlet air $T_{air}$ that cools the device by convection air flow; and compensating for changes in $T_{air}$ by varying a convection coefficient (h) which is a function of air velocity to maintain a product of $h*\Delta T$ at a constant value; wherein $\Delta T$ is a temperature differential between the device ($T_{AD}$) and $T_{air}$.

Further aspects of the invention are disclosed herein. The above discussed and other features and advantages of the present invention will be appreciated and understood by those skilled in the art from the following detailed description and drawings.

BRIEF DESCRIPTION OF THE DRAWINGS

Referring to the exemplary drawings wherein like elements are numbered alike in the several Figures.

DETAILED DESCRIPTION OF THE INVENTION

Figure 1:
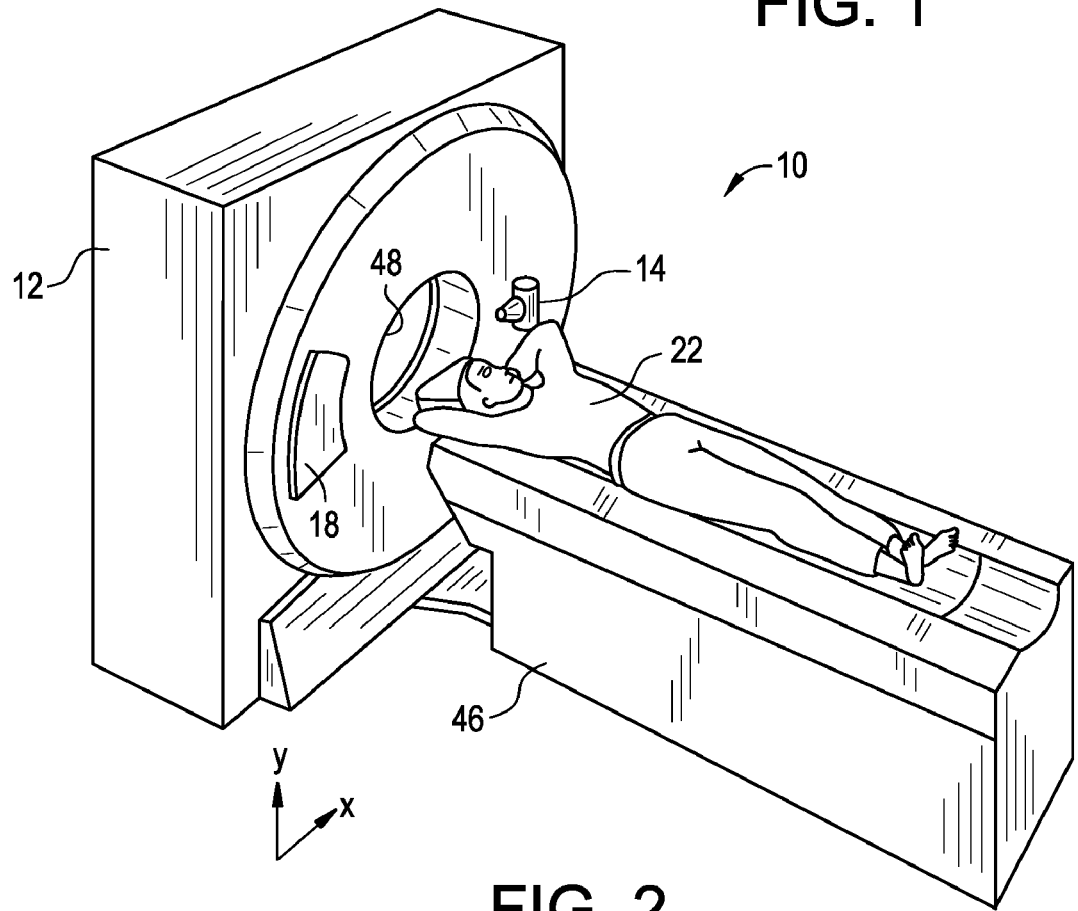
FIG. 1 is a pictorial view of a CT imaging system according to the present invention.

Referring to FIG. 1, a computed tomography (CT) imaging system 10 is shown as including a gantry 12 representative of a "third generation" CT scanner. The gantry 12 has an x-ray source 14 that projects a beam of x-rays 16 toward a detector array 18 on the opposite side of the gantry 12.

The detector array 18 is formed by a plurality of detection elements 20 which together sense the projected x-rays that pass through a medical patient 22. Each detection element 20 produces an electrical signal that represents the intensity of an impinging x-ray beam and hence, the attenuation of the beam as it passes through the patient 22. During a scan to acquire x-ray projection data, the gantry housing 12 and the components mounted thereon rotate about a center of gravity or axis 24.

The operation of the x-ray source 14 is governed by a control mechanism 26 of the CT system 10. The control mechanism 26 includes an x-ray controller 28 that provides power and timing signals to the x-ray source 14. A data acquisition system (DAS) 32 in the control mechanism 26 samples analog data from the detection elements 20 and converts the data to digital signals for subsequent processing. An image reconstructor 34 receives sampled and digitized x-ray data from the DAS 32 and performs high speed image reconstruction. The reconstructed image is applied as an input to a computer 36 which stores the image in a mass storage device 38.

The computer 36 also receives and supplies signals via a user interface or graphical user interface (GUI). Specifically, the computer 36 receives commands and scanning parameters from an operator console 40 that preferably includes a keyboard and mouse (not shown). An associated cathode ray tube display 42 allows the operator to observe the reconstructed image and other data from the computer 36. The operator supplied commands and parameters are used by the computer 36 to provide control signals and information to the x-ray controller 28, the DAS 32, and a table motor controller 44 in communication with a table 46 to control operation of and movement of the system components.

Figure 2:
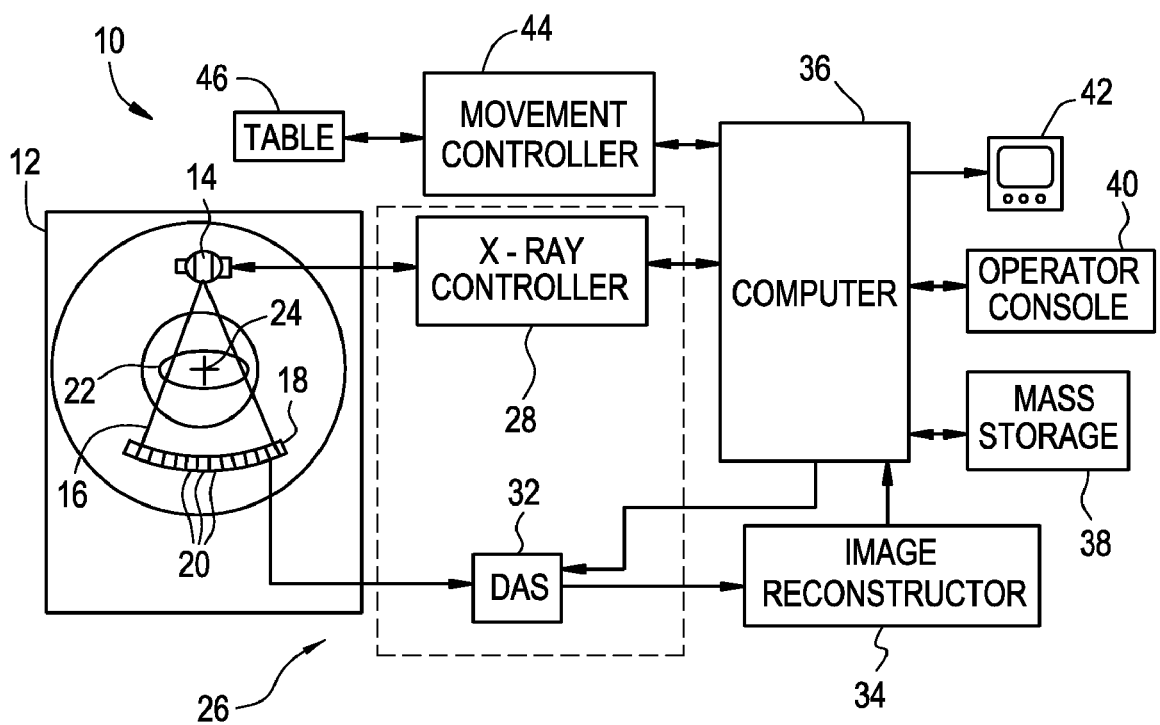
FIG. 2 is a block schematic diagram of the system illustrated in FIG. 1.
Figure 3:
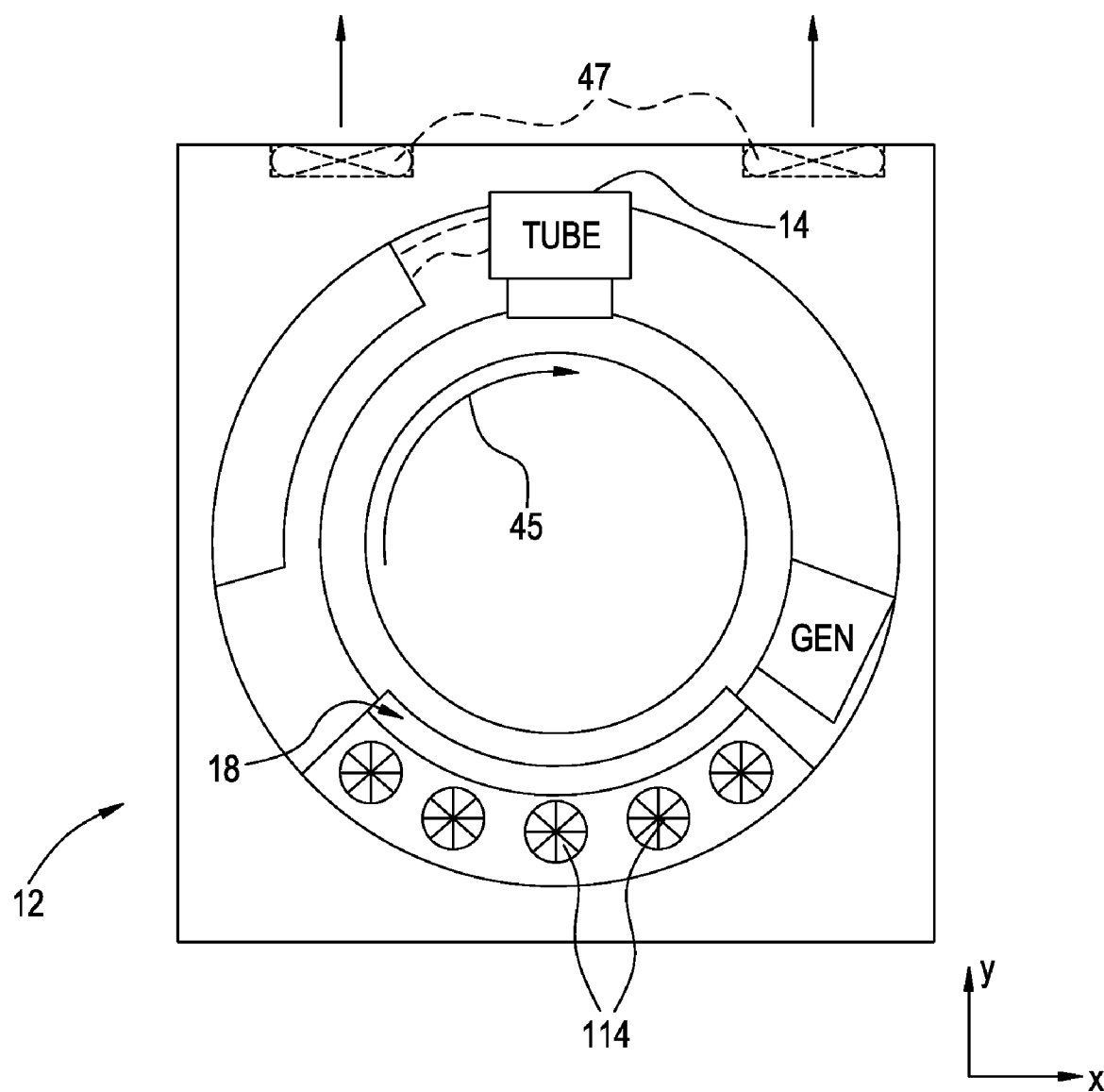
FIG. 3 is a schematic diagram of a variable speed fan in fluid communication with an A/D module having feedback control using a first temperature sensor configured to measure an inlet air temperature ($T_{air}$) in accordance with an exemplary embodiment.

FIG. 3 illustrates a cross section view of gantry 12 in an X-Y plane relative to the perspective view of FIG. 1. Gantry 12 has an x-ray tube 14 that projects a beam of x-rays 16 (FIG. 2) toward detector array 18 on the opposite side of the gantry 12. Detector array 18 includes an analog/digital (A/D) board or module (not shown) that heats up during operation and is cooled with a plurality of fans 114 (5 shown) on the opposite side of gantry 12 proximate detector array 18. As gantry 12 rotates in a direction indicated generally with arrow 45, detector array 18 and plurality of fans 114 rotate in the same direction. Cooling air drawn in by fans 114 is exhausted using fans 47.

Figure 4:
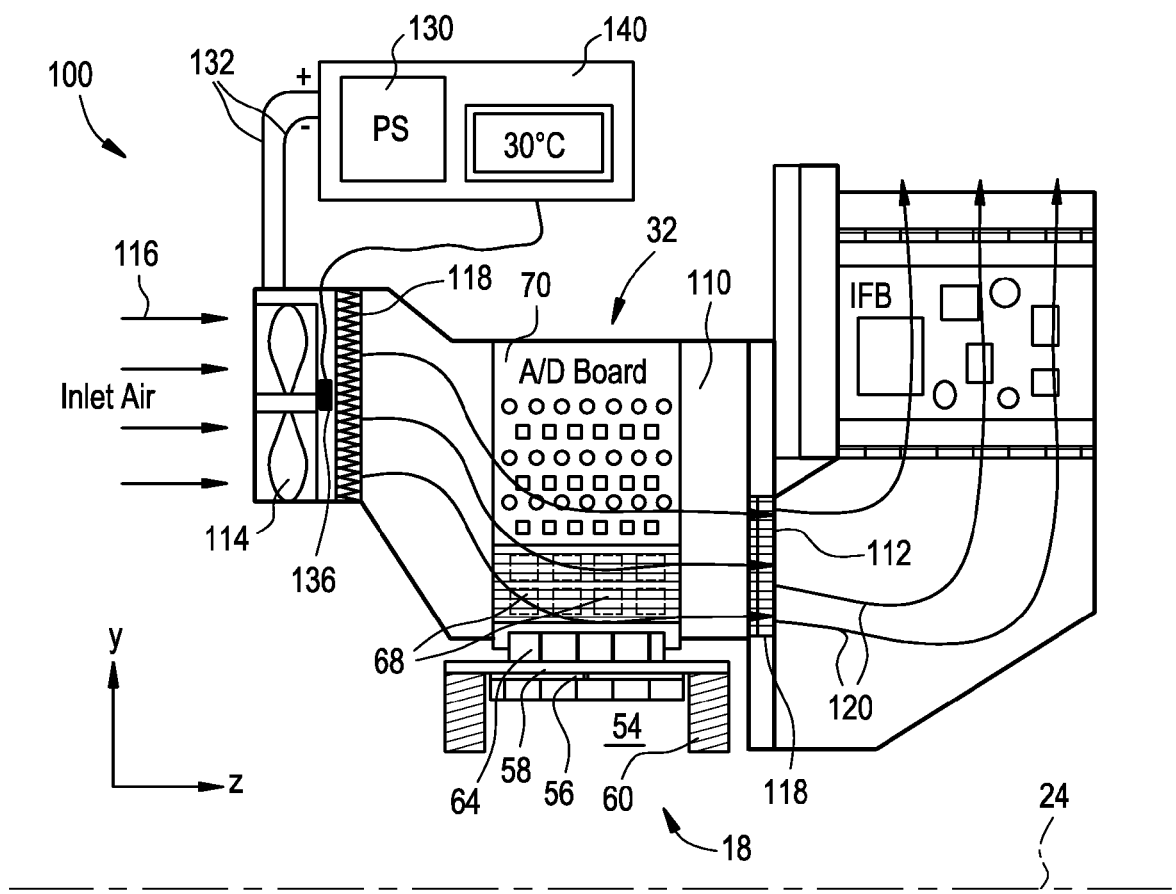
FIG. 4 is a schematic diagram of the variable speed fan in fluid communication with an A/D module of FIG. 3 having further feedback control using a second temperature sensor configured to measure a temperature of the A/D module ($T_{AD}$) in accordance with another exemplary embodiment.

Referring now to FIG. 4, DAS 32 operably coupled to detector array 18 and in thermal communication with variable speed fan system 100 is illustrated in accordance with an exemplary embodiment. In the construction shown in FIG. 4, a plurality of detectors 18, e.g. 1 detector, is assembled into a module 54. Although not shown, each detector 18 comprises a scintillating crystal disposed on a semiconductor diode 56. The latter, in turn, is supported on a substrate 58, of which is attached to a pair of opposing detector rails 60 preferably made of a material with high thermal conductivity such as, for example, aluminum. A matching crystal is attached so as to illuminate the respective diodes 56. Both attachments may be by a thin layer of epoxy or other cement. A multi-conductor cable 64 may be soldered to the diode output leads on substrate 58 so as to provide an electrical output from each detector to a computer or control mechanism 26 for data storage and image generation. As described above, the output from each diode 56 outputs an electrical analog signal to an analog/digital (A/D) converter 68 disposed on an application specific integrated circuit (ASIC) A/D module 70 to convert the analog signal to a digital signal for processing by the computer.

In a CT or CAT scanner of the third generation type, x-ray source 14 and the array of x-ray detectors 18 are rotated in a scanning plane about axis 24 in which is located the patient object. X-rays from the source pass from a source point, commonly referred to as the focal spot, through the object and are received by individual detectors 18.

Still referring to FIG. 4, DAS 32 is disposed in a plenum 110 defined by a housing 112 of a variable speed fan system 100. Variable speed fan system 100 includes housing 112 further defining plenum 110 in which DAS 32 is disposed. Housing 112 further includes a fan 114 disposed therein configured to draw ambient air generally indicated at 116 and direct ambient air 116 through plenum 110 across A/D module 70 disposed in plenum 110. Plenum 110 is defined by a pair of walls 118 extending from opposing sides of housing 112. Air 116 cools A/D module 70 using convection and heated air generally indicated at 120 exits housing 112.

The cooling of the A/D modules or cards 70 can be described by the following equations:

$$Q = HA\Delta T \quad \text{(eq. 1)}$$

where,

Q=heat to be removed from ASICs to prevent heating of corresponding diodes h=convection coefficient which is a strong function of local air velocity ~V0.8 and a weak function of air temperature (i.e., can be ignored)

A=Surface area for heat exchange (fixed value)

$\Delta T$=(TAD−Tair) (temperature of A/D board ASIC to be cooled minus cooling air temperature).

Since the power output of the ASICS or A/D module 70 does not vary with time, equation 1 can be re-arranged to give:

$$\frac{Q}{A} = h\Delta T \text{ where} \quad \text{(eq. 1)}$$

$\frac{Q}{A}$ is the amount of heat removed per unit area.

Thus, changes in inlet air temperature can be compensated by varying the convection coefficient (h) through compensation of air velocity to maintain the product of h*$\Delta T$ at a constant value. Since h is a strong function of air velocity and realization that h is very weak function of air temperature, and thus can be ignored, air velocity can be proportionally varied to preserve the product of h*$\Delta T$.

Referring again to FIG. 4, the air velocity can be varied by varying the speed of fan 114. Fan 114 is operably coupled to a power supply 130 via power cables 132 configured to provide a variable current to fan 114. A temperature sensor 136 is disposed proximate fan 114 to sense a temperature of the cooling air ($T_{air}$) or inlet air 116. Inlet air 116 has a temperature of 30° C. as illustrated in FIG. 3 (i.e, $T_{air}$=30° C.). A temperature signal from temperature sensor 136 is inputted to controller 140 in operable communication with power supply 132 to vary a current supplied to fan 114 to vary a speed thereof.

Various types of variable speed fans systems are utilized in the art. One common approach is to utilize a thermistor for temperature sensor 136 within the proximity of fan 114 to detect changing air temperature inside housing 112 and then vary the fan speed accordingly.

In one embodiment, a brushless DC fan whose speed is directly proportional to a supplied DC voltage, or alternatively current, level provided from power supply 130. A feedback signal indicative of the speed of variable speed fan 114 is, in turn, may be provided to controller 140 to complete a closed loop control system.

Alternatively, it is envisioned that the temperature signal acquired by the temperature sensor 136 is inputted to controller 140 and converted into digital value. The controller 140 may include an integrated circuit (IC) chip which has the function of digitizing signals detected by temperature sensor 136 in order to detect an abnormal temperature or a change in temperature. The temperature value is then stored in memory.

Controller 140 may include a program for fan control that is executed at a constant time interval so that a proper rotational frequency of the fan is determined by extracting necessary temperature value from the memory. Controller 140 may include, but is not limited to, a pulse width modulation (PWM) controller 140. The value of the determined rotational frequency of the fan is inputted into the PWM controller 140. PWM is a kind of pulse modulation scheme in which modulation is made by varying the pulse width in accordance with the signal while keeping the magnitude of the pulse amplitude. The controller may be supplied as a discrete IC, but can be supported normally in a super I/O chip (semiconductor which supports serial, parallel, key board, mouse signals, etc.) of the computer system 36. The rotational frequency of the fan can be changed continuously by turning on/off the power supply for the fan 114 by a PWM scheme. Thus, a more continuous and flexible fan control is possible instead of a control using only specific rotational frequencies which may be fixedly determined in accordance with the thresholds of the detected temperature.

In order to convert the output signal of the PWM controller 140 into an ON/OFF current signal for the fan drive, a current drive element (for example, a transistor) can be provided for each fan. The rotational frequency of the fan 114 is finally controlled in accordance with this output.

It will be recognized that a speed of fan 114 may be varied a number of other ways using feedback of the cooling air temperature to control a speed of fan 114 and thus preserve the product of h*$\Delta T$. It should be noted that $T_{AD}$ considered to be a fixed value based on the above assumption that power output of A/D module 70 does not vary with time in this scheme. Furthermore, it will be recognized that the above system and method do not compensate for fan efficiency due to rotation of gantry 12.

Figure 6:
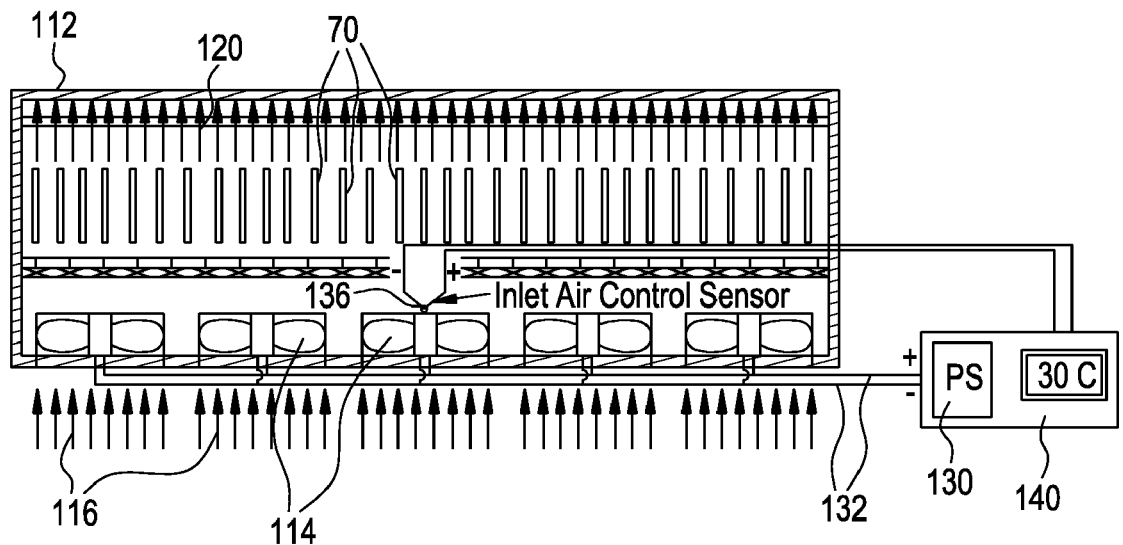
FIG. 6 is a schematic diagram of the variable speed fans in fluid communication with the A/D modules of FIG. 5 having further feedback control using a second temperature sensor configured to measure a temperature of the A/D module ($T_{AD}$) in accordance with another exemplary embodiment.

FIG. 6 illustrates power supply 130 and controller 140 in operable communication with a plurality of fans 114 providing cooling air 116 to a plurality of A/D modules 70 disposed in a single housing 112. In this embodiment, temperature sensor 136 provides a feedback control for coherently varying a speed of fans 114. However, it will be recognized that each fan 114 or contiguous fans may receive feedback control from a corresponding temperature sensor 136, thus increasing the amount of control of air velocity associated with corresponding A/D modules 70 being cooled.

To compensate for changes in fan efficiency due to rotational effects this same strategy can be employed by feeding back a suitable temperature such as the board temperature near the A/D module 70 or temperature near diodes 56. It will be recognized that a fan works optimally when air is normal relative to the fan blades. Thus, as the air flow changes due to changes in fan efficiency (e.g., due to rotation of gantry 12) the temperature of A/D module 70 will change from lack of cooling air flow. For example, if the inlet air 116 temperature is maintained ($T_{air}$=constant) as gantry 12 is rotated, a temperature of the A/D module 70 increases because the efficiency of fan 114 decreases when rotated. From knowledge of the temperature of A/D module ($T_{AD}$), or other available temperature for which a transfer function back to the diodes 56 can be constructed, and the inlet air temperature ($T_{air}$), a $\Delta T$ can be determined and the air flow rate can be adjusted to preserve the product of h*$\Delta T$, since $\Delta T = (T_{AD} - T_{air})$.

Figure 5:
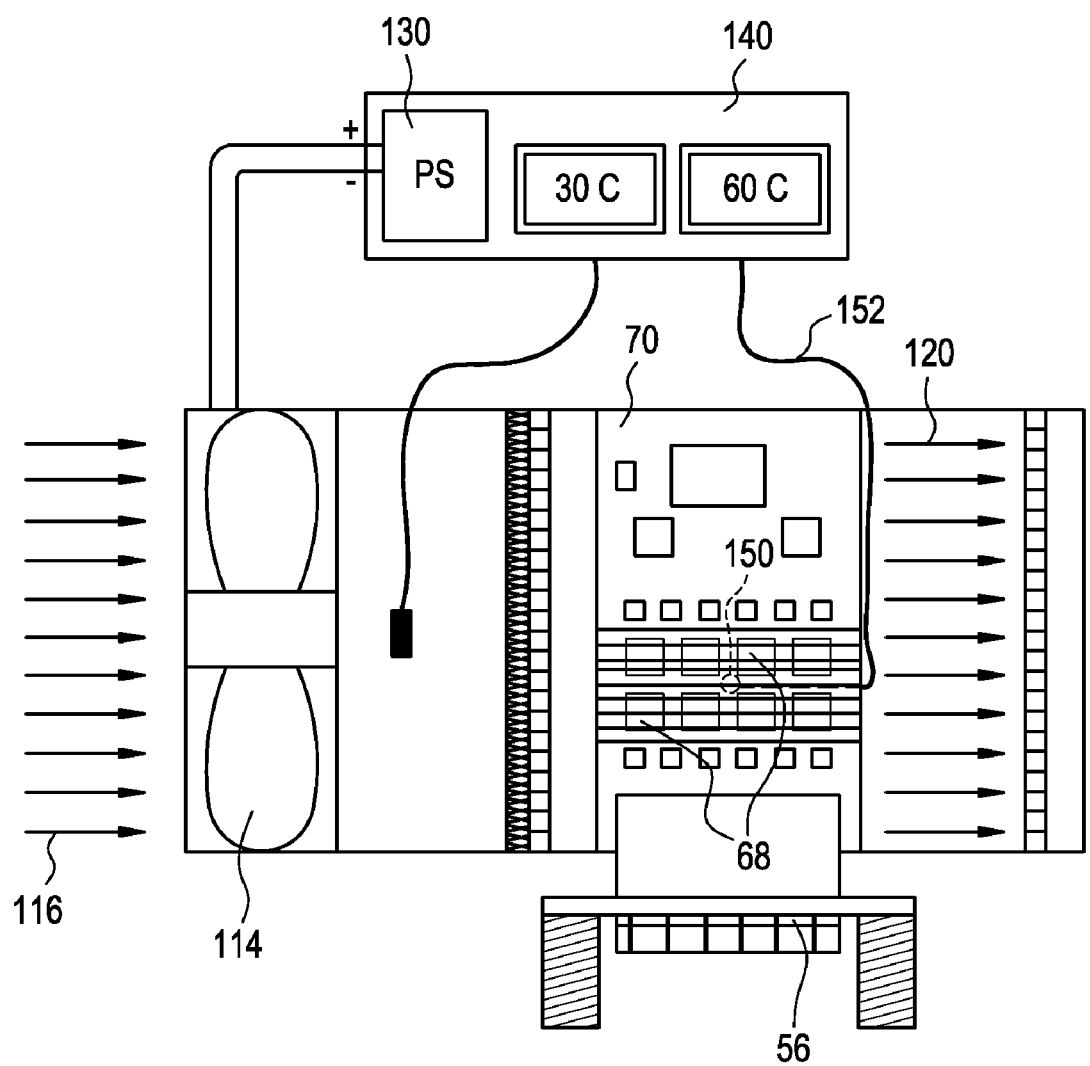
FIG. 5 is a schematic diagram of a plurality of variable speed fans in fluid communication with a plurality of A/D modules having feedback control using a first temperature sensor configured to measure an inlet air temperature ($T_{air}$) in accordance with an exemplary embodiment.

Referring now to FIG. 5, the variable speed fan system 100 of FIG. 4 is illustrated with a temperature sensor 150 in thermal communication with A/D converters 68 disposed on an A/D module 70. Temperature sensor 150 provides a temperature signal via line 152 to controller 140 much like that described above with respect to temperature sensor 136. In this manner, controller 140 can determine $\Delta T$ to adjust the air flow rate to preserve the product of h*$\Delta T$ when the fan efficiency decreases due to rotation of gantry 12 about axis 24. FIG. 4 illustrates inlet air 116 has a $T_{air}$ temperature of 30° C. while a temperature of A/D module 70, $T_{AD}$ is 60° C., thus, $\Delta T=30°$ C.

This value of $\Delta T$ is used by controller 140 to determine a speed of fan 114 to preserve a product of h*$\Delta T$, since h is dependent on air velocity as discussed above. For example, as $\Delta T$ increases, h decreases by increasing a speed of fan 114.

Figure 7:
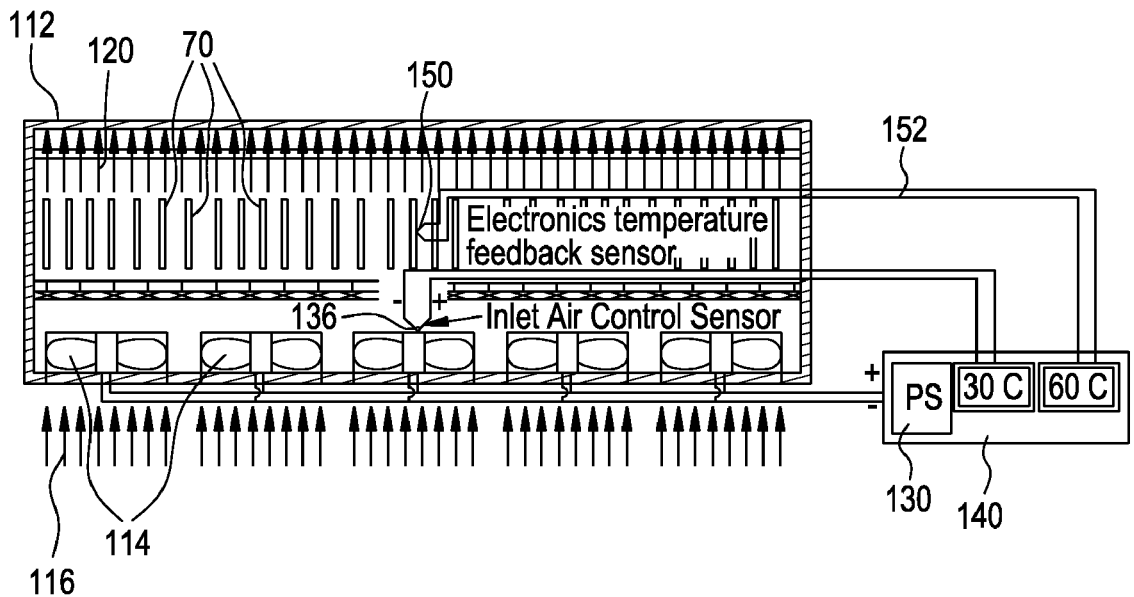
FIG. 7 is a graph of a reduction in fan noise versus fan speed illustrating a reduction of fan noise as a function of speed reduction percentage.

FIG. 7 illustrates power supply 130 and controller 140 operable communication with a plurality of fans 114 providing cooling air 116 to a plurality of A/D modules 70 disposed in a single housing 112. In this embodiment, temperature sensors 136 and 150 provide a feedback control for coherently varying a speed of fans 114. However, it will be recognized that each fan 114 or contiguous fans may receive feedback control from individual corresponding temperature sensors 136 and 150, thus increasing the amount of control for air velocity associated with corresponding A/D modules 70 being cooled.

Figure 8:
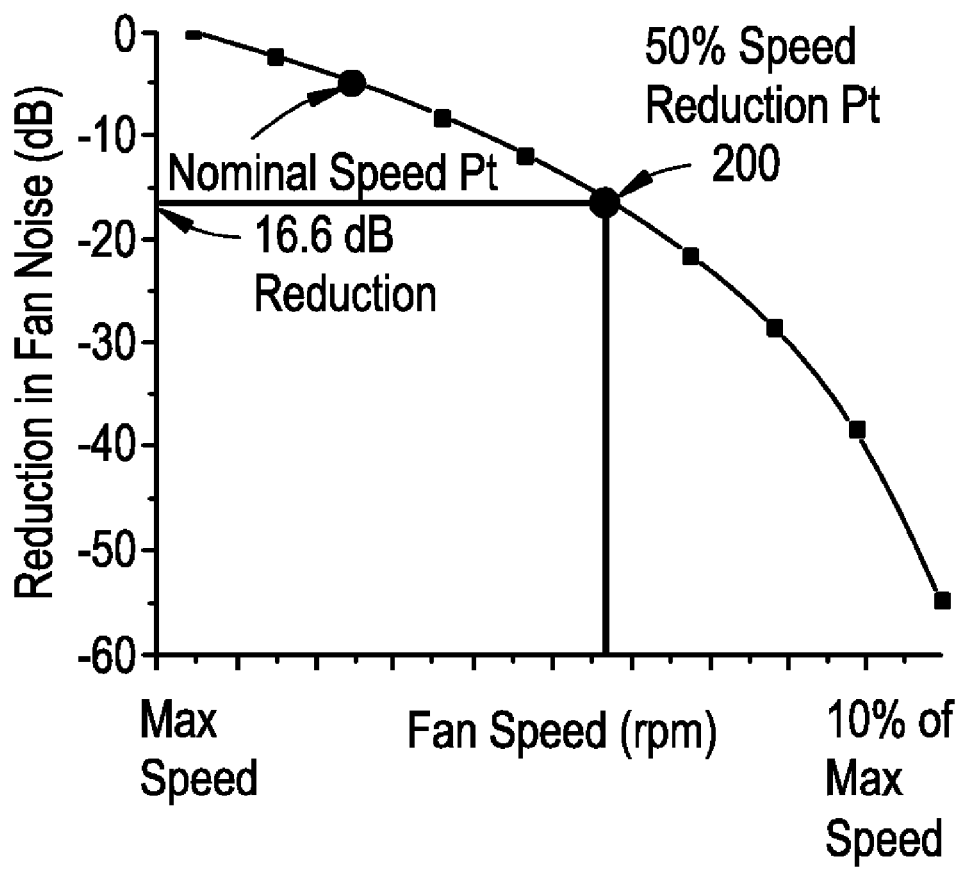

Referring now to FIG. 8, it will be recognized by one skilled in the pertinent art that the above described feedback control can be utilized to match cooling air flow rate to cooling needs to lower audible noise of fan 114. The change in noise power of a fan is proportional to the log of the ratio of the change in rotational speed. i.e, $$\frac{DB2}{DB1} = 55 * LOG\left(\frac{N2}{N1}\right) \qquad (eq. 3)$$

Equation 3 is a fan law equation describing the ratio of audible noise to a ratio of fan speed. At normal operating and idle conditions, a CT room and hence the gantry ambient temperature are stable and in a middle temperature range. At the extreme operating conditions, i.e., cold CT room and hot CT room, the fans need to operate at lower and higher speeds, respectively. Thus at typical operating conditions, the fans can operate at reduced speeds and thus reduced noise levels.

For example, FIG. 8 illustrates that when fan 114 reduces speed from a 100% maximum speed to a 50% speed reduction point indicated generally at 200, there is a reduction in fan noise of about 16.6 dB.

Figure 9:
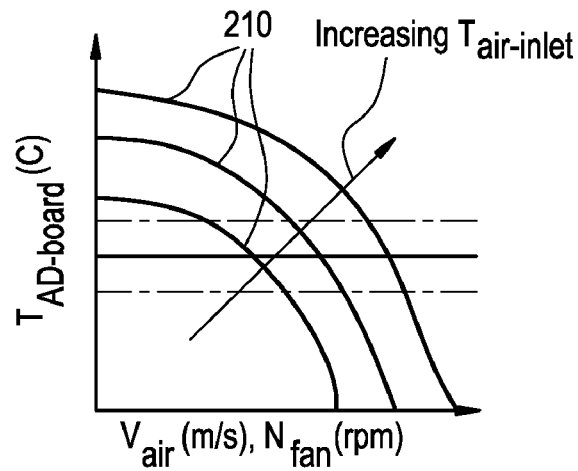
Figure 10:
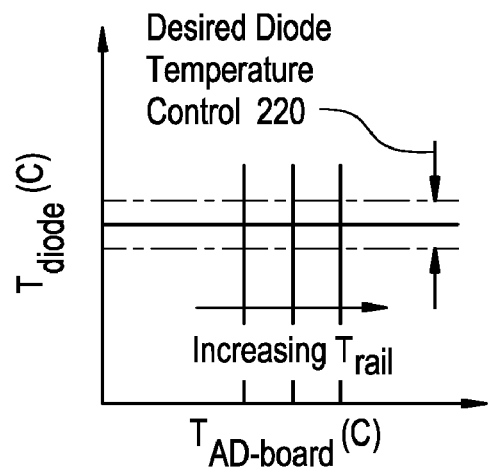
Figure 11:
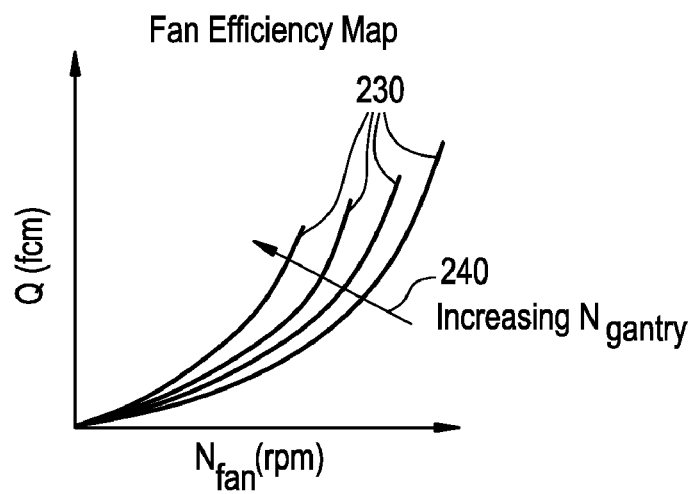

Referring now to FIGS. 9–11, three general performance/control maps are illustrated. FIG. 9 illustrates that as either the velocity of air inlet or the fan speed or revolutions increase, the temperature of the A/D module 70 decreases. FIG. 9 depicts three different plots 210 representing three different temperatures of the inlet air 116 ($T_{air-inlet}$). FIG. 10 illustrates that in order to hold diodes 56 at a desired temperature indicated generally by a range 220, it is necessary to hold both rails 60 and A/D module 70 to constant temperature values. FIG. 11 is a fan efficiency map of heat to be removed (Q) versus the number of fan revolutions per minute ($N_{fan}$). FIG. 11 further illustrates four plots 230 of fan efficiency with respect to increasing a gantry speed of revolution indicated at 240. FIG. 11 shows that as the gantry speed increases, the speed of the fans need to increase to remove the same amount of heat (Q) since the fan efficient decreases as the speed of the gantry increases.

An embodiment of the present invention improves and potentially solves the very difficult problem of gantry ambient temperature control through feedback control using at least a temperature of inlet air. This solution is much less expensive than a system level air conditioning system to cool the DAS and detectors. An embodiment of the present invention also offers a simple means of compensating for fan performance changes due to gantry rotation which is continually increasing in speed with each generation of CT machine. By controlling air flow, a temperature of the A/D module can be maintained within a predetermined range and the photo diodes of the detector assembly thermally coupled to the A/D module can also be maintained within a predetermined range. An embodiment of the present invention potentially offers huge reductions in audible noise via reduced fan rotation speeds by matching air flow rate to cooling requirements. Lastly, by using a temperature of the A/D module or a temperature at or near the photo diode, changes in air density due to altitude are automatically accounted for.

In previous embodiments the detector rail temperature was neglected from the control scheme because the detector rail temperature was assumed to be held constant by another control system. In the case where the rail temperatures cannot be held constant, all of the above embodiments still work satisfactorily if the rail temperature is monitored and a corresponding change to the fan speed is commanded by the control system to compensate for the varying rail temperatures.

An alternative embodiment of this invention would be to use the photo diode to measure it's own temperature by calibrating the photo diode and storing this information in the CT system. By using the photo diode to provide the control temperature feedback, the fans could be varied to control the photo diodes directly. Such a system would work whether the electronic power output was constant or variable. In such a configuration, neither the power output of the A/D modules nor the inlet cooling air need to be constant. Such a system would also self compensate for cooling air temperature and changes in air density due to altitude.

Figure 12:
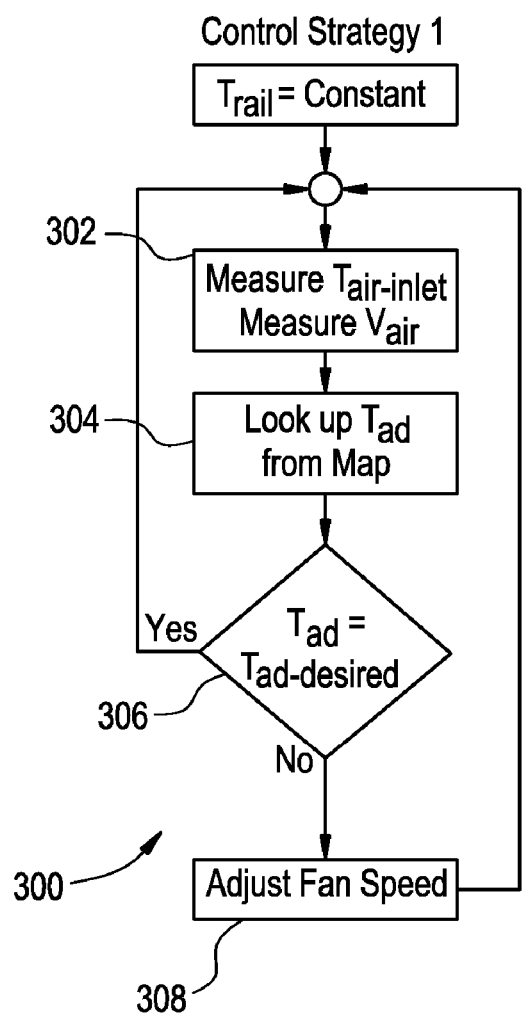

Referring now to FIGS. 12-15, four control routines are illustrated for adjusting fan speed in order to maintain a temperature of the A/D module 70 ($T_{AD}$) (FIGS. 12–14) or a temperature of diode 56 ($T_{diode}$) (FIG. 15) constant diode FIG. 12 illustrates a control routine 300 where a temperature of detector rail 60 ($T_{rail}$) is constant. Routine 300 includes measuring air inlet temperature ($T_{air-inlet}$) and velocity of air inlet ($V_{air}$) (e.g., speed of fan 114) at block 302. Then determine a temperature of A/D module 70 ($T_{ad}$) mapped in a look up table at block 304. If $T_{ad}$ is equal to a desired temperature of the A/D module ($T_{ad-desired}$) at block 306, then block 302, if not, then block 308 to adjust fan speed.

Figure 13:
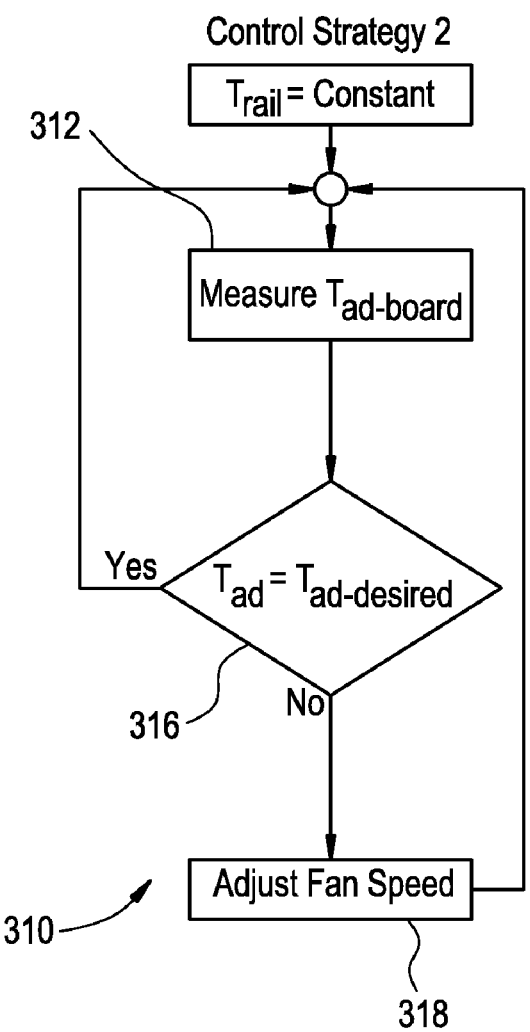

FIG. 13 illustrates a control routine 310 where a temperature of detector rail 60 ($T_{rail}$) is constant. Routine 310 includes measuring a temperature of A/D module 70 ($T_{ad-board}$) at block 312. If T is equal to a desired temperature of the A/D module ($T_{ad-desired}$) at block 316, then block 312, if not, then block 318 to adjust fan speed.

FIG. 14 illustrates a control routine 320 where a temperature of detector rail 60 ($T_{rail}$) is variable. Routine 320 includes measuring a temperature of A/D module 70 ($T_{ad-board}$) and a temperature of detector rail 60 ($T_{rail}$) at block 322. Then determine a temperature of A/D module 70 ($T_{ad}$) mapped in a look up table at block 324. If $T_{ad}$ is equal to a desired temperature of the A/D module ($T_{ad-desired}$) at block 326, then block 322, if not, then block 328 to adjust fan speed.

FIG. 15 illustrates a control routine 340 where a temperature of detector rail 60 ($T_{rail}$) is constant or variable. Routine 340 includes measuring a temperature of diode 56 ($T_{diode}$) at block 342. If $T_{diode}$ is equal to a desired temperature of the diode 56 (T$_{diode-desired}$) at block 346, then block 342, if not, then block 348 to adjust fan speed.

As described above, the embodiments of the invention may be embodied in the form of computer-implemented processes and apparatuses for practicing those processes. Embodiments of the invention may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. An embodiment of the present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof with-out departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

The invention claimed is:

1. A method for variable speed fan control for thermal management of a device, the method comprising:
   disposing a first temperature sensor proximate a variable speed fan;
   measuring an air temperature of inlet air T$_{air}$ that cools the device by convection air flow; and
   configuring a controller to compensate for changes in T$_{air}$ by varying a convection coefficient h which is a function of air velocity to maintain a product of h*$\Delta$T at a constant value;
   wherein $\Delta$T is a temperature differential between the device T$_{AD}$ and T$_{air}$.

2. The method of claim 1 further comprising:
   varying h in accordance with changes in T$_{air}$ by varying an air velocity across the device by varying a speed of the variable speed fan.

3. The method of claim 2 wherein said T$_{AD}$ is presumed a constant value since a power output of said device does not vary with time, therefore a speed of said fan is directly proportional to said Tair.

4. The method of claim 1 further comprising:
   disposing a second temperature sensor proximate said device to measure said T$_{AD}$.

5. The method of claim 4 wherein said second temperature sensor compensates for changes in fan efficiency.

6. The method of claim 5 wherein said fan efficiency varies due to rotation of said fan about an axis different from a fan blade axis of rotation.

7. The method of claim 6 wherein said axis is an axis of gantry rotation for a CT scanner.

8. The method of claim 1 wherein said product of $$h*\Delta T = \frac{Q}{A},$$

where Q is heat to be removed from said device and A is a surface area for heat exchange from said device.

9. The method of claim 8 wherein said $$\frac{Q}{A}$$

is a constant value since area of heat exchange is a fixed value and since a power output of said device does not vary with time.

10. The method of claim 1 wherein said device is an A/D module of a CT scanner for a data acquisition system (DAS) in operable communication with a plurality of detectors.

11. The method of claim 10 wherein said fan includes a plurality of fans disposed within a gantry housing of the CT scanner.

12. The method of claim 10 further comprising:
    disposing a second temperature sensor proximate said device to measure said T$_{AD}$, wherein said second temperature sensor includes direct temperature feedback from a photo diode of the plurality of detectors used to control the plurality of fans.

13. A method for variable speed fan control for thermal management of a A/D card in an imaging system, the method comprising:
    disposing a variable speed fan configured to convectively cool the A/D card for the CT scanner for a data acquisition system (DAS) in operable communication with a plurality of detectors;
    disposing a first temperature sensor proximate said variable speed fan;
    measuring an air temperature of inlet air T$_{air}$ that cools said A/D card by convection air flow; and
    configuring a controller to compensate for changes in T$_{air}$ by varying a convection coefficient h which is a function of air velocity to maintain a product of h*$\Delta$T at a constant value;
    wherein $\Delta$T is a temperature differential between the A/D card T$_{AD}$ and T$_{air}$.

14. The method of claim 13 further comprising:
    varying h in accordance with changes in T$_{air}$ by varying an air velocity across the A/D card by varying a speed of said variable speed fan.

15. The method of claim 13 further comprising:
    disposing a second temperature sensor proximate said A/D card to measure said T$_{AD}$.

16. The method of claim 15 wherein said second temperature sensor compensates for changes in fan efficiency, said fan efficiency varies due to rotation of said fan about an axis different from a fan blade axis of rotation, said axis is an axis of gantry rotation for a CT scanner.

17. The method of claim 15 wherein said second temperature sensor includes direct temperature feedback from a photo diode of the plurality of detectors.

18. The method of claim 13 wherein said product of $$h * \Delta T = \frac{Q}{A},$$

where Q is heat to be removed from said device and A is a surface area for heat exchange from said device.

19. The method of claim 18 wherein said $$\frac{Q}{A}$$

is a constant value since area of heat exchange is a fixed value and since a power output of said device does not vary with time.

20. A system for variable speed fan control, the system comprising:
a housing defining an air inlet and air outlet and a plenum intermediate said air inlet and said air outlet;
an electronic circuit card disposed in said plenum;
a variable speed fan disposed between said air inlet and said plenum, said fan configured to draw air in through said air inlet over said card and out said outlet to cool said card;
a first temperature sensor disposed proximate said fan to measure an inlet air temperature Tair; and
a controller in operable communication with said first temperature sensor and a power supply powering said fan;
wherein a change in said $T_{air}$ can be compensated for by varying a velocity of said air by changing a speed of said fan.

21. The system of claim 20 wherein changes in said $T_{air}$ are compensated by varying a convection coefficient h through said air velocity to maintain a product of h*ΔT at a constant value.

22. The system of claim 21 wherein said ΔT is a temperature associated with said card $T_{AD}$ minus $T_{air}$.

23. The system of claim 22 wherein said $T_{AD}$ is presumed a constant value since a power output of said card does not vary with time, therefore a speed of said fan is directly proportional to said Tair.

24. The system of claim 21 further comprising:
a second temperature sensor disposed proximate said card to measure said $T_{AD}$.

25. The system of claim 24, wherein said second temperature sensor includes direct temperature feedback from a photo diode of the plurality of detectors.

26. The system of claim 24 wherein said second temperature sensor compensates for changes in fan efficiency.

27. The system of claim 26 wherein said fan efficiency varies due to rotation of said fan about an axis different from a fan blade axis of rotation.

28. The system of claim 27 wherein said axis is an axis of gantry rotation for a CT scanner.

29. The system of claim 21 wherein said product of $$h * \Delta T = \frac{Q}{A},$$

where Q is heat to be removed from said card and A is a surface area for heat exchange from said card.

30. The system of claim 29 wherein said $$\frac{Q}{A}$$

is a constant value since area of heat exchange is a fixed value and since a power output of said card does not vary with time.

31. A computer program product for variable speed fan control for thermal management of a device, the product comprising:
a storage medium readable by a processing circuit and storing instructions for execution by the processing circuit for:
reading a first temperature sensor proximate a variable speed fan, said sensor configured to measure an air temperature of inlet air $T_{air}$ that cools the device by convection air flow; and
compensating for changes in $T_{air}$ by varying a convection coefficient h which is a function of air velocity to maintain a product of h*ΔT at a constant value;
wherein ΔT is a temperature differential between the device $T_{AD}$ and $T_{air}$.

* * * * *

UNITED STATES PATENT AND TRADEMARK OFFICE
CERTIFICATE OF CORRECTION

PATENT NO. : 7,102,308 B2
APPLICATION NO. : 10/710213
DATED : September 5, 2006
INVENTOR(S) : Joseph James Lacey et al.

It is certified that error appears in the above-identified patent and that said Letters Patent is hereby corrected as shown below:

Column 5,
Line 4, after "Q=" delete "*H*" and insert therefor -- *h* --.

Column 6,
Line 24, after "$T_{AD}$" insert -- is --.

Column 7,
Line 1, after "illustrates" insert -- that --.
Line 10, before "operable" insert -- in --.

Column 8,
Line 52, after "If" delete "T" and insert therefor -- $T_{ad\text{-}board}$ --.

Column 9,
Line 27, after "thereof" delete "with-out" and insert therefor -- without --.

Signed and Sealed this

Ninth Day of January, 2007

JON W. DUDAS
*Director of the United States Patent and Trademark Office*